United States Patent [19]

Tewari

[11] Patent Number: 5,654,161

[45] Date of Patent: Aug. 5, 1997

[54] METHOD FOR DIAGNOSING PROSTATE CANCER

[75] Inventor: Prakash C. Tewari, Mansfield, Mass.

[73] Assignee: Chiron Diagnostics Corporation, Walpole, Mass.

[21] Appl. No.: 439,922

[22] Filed: May 12, 1995

[51] Int. Cl.$^6$ .................. G01N 33/574; G01N 33/53
[52] U.S. Cl. .................. 435/7.23; 435/7.9; 435/7.92; 436/64; 436/813
[58] Field of Search .................. 435/7.23, 7.9, 435/7.92; 436/64, 813

[56] References Cited

FOREIGN PATENT DOCUMENTS

| | | |
|---|---|---|
| 0 594 873 | 5/1996 | European Pat. Off. . |
| 43 22 342 | 2/1995 | Germany . |
| WO92/01936 | 2/1992 | WIPO . |
| WOA9322676 | 11/1993 | WIPO . |
| WOA9518381 | 7/1995 | WIPO . |

OTHER PUBLICATIONS

Pettersson, et al., *Clinical Chemistry*, vol. 41, No. 10, pp. 1480–1488, 1995.
Demura, et al., *Cancer*, vol. 77, No. 6, pp. 1137–1143, 1996.
Bluestein et al, Journal of Tumor Marker Oncology, 7:41–60, 1992.
Chandra et al, Biochemistry 22:5055–5060, 1983.
Chirarodo, A., Cancer Research 51:2498–2505, 1991.
Christensson et al, Journal of Urology 150:100–105, 1993.
Hill et al, Nature 311:175–177, 1984.
Hinds et al, Neurobiology of Aging 15:21–27, 1994.
Hwang et al, Proc. Natl. Acad. Sci. USA 91:9579–9583, 1994.
Keesee et al, Proc. Natl. Acad. Sci USA 91:1913–16, 1994.
Laurell et al, The Plasma Proteins, Structure, Function and Genetic Control. Ed. Putnam FW, pp. 229–264, 1975. Academic Press, NY.
Leinonen et al, Clinical Chemistry 39:2098–2103, 1993.
Lilja, H., Scand. Journal of Laboratory Investigation 55 Supplement:47–56, 1995.
Lilja et al, Cancer supplement 70(1):230–234, 1992.
Lilja et al, Clin Chem. 37:1618–25, 1991.
Lindmark et al, Biochimica et Biophysica Acta 997:90–95, 1989.
Rubin, H., Biol. Chem. Hoppe–Seyler 373:497–502, 1992.
Rubin et al, Journal of Biological Chemistry 265:1199–1207, 1990.
Sensabaugh et al, Journal of Urology 144:1523–1526, 1990.
Stenman et al, Cancer Research 51:222–226, 1991.
Wang et al, Methods in Cancer Research, vol. XIX:179–197, 1982. Academic Press, NY.
Wilson, M.J., Microscopy Research and Technique 30:305–318, 1995.
Wu et al, Journal of Clinical Laboratory Analysis 9:25–31, 1995.
Zhou et al, Clinical Chemistry 39:2483–2491, 1993.

*Primary Examiner*—Toni R. Scheiner
*Attorney, Agent, or Firm*—Arthur S. Morgenstern; Helen Greer; Robert P. Blackburn

[57] ABSTRACT

A method for diagnosing prostate cancer in a mammal is described. Serum from a mammal is provided. PSA is added to this serum, and the amount of ACT-PSA complex formed is measured. It is determined if the mammal has prostate cancer based on the amount of ACT-PSA complex that is formed. An isolated prostate cancer specific form of ACT which is capable of forming a stable complex with PSA is also described.

12 Claims, 3 Drawing Sheets

METHOD FOR DIAGNOSING PROSTATE CANCER

FIELD OF THE INVENTION

This invention relates to methods of diagnosing prostate cancer, and measuring prostate cancer specific forms of α1-antichymotrypsin (ACT).

BACKGROUND OF THE INVENTION

Prostate cancer is a widespread medical problem. Histological evidence of prostate cancer occurs in an estimated 30–40% of men over the age of 50, yet only 9% of men develop clinical signs or symptoms of prostate cancer and 3% die from the disease each year. (Chirarodo, 1991) Early prognosis often can prolong the longevity of the patient. Diagnosis and monitoring of prostate cancer, however, has been problematic. One method that has been used is to measure the amount of prostate specific antigen (PSA) in the serum of patients, given that there appears to be some correlation between increased levels of PSA and the presence of prostate cancer. The benefits of such serum PSA measurements, however, are controversial because of the rather low specificity of this test. Lilja et at., Cancer Supplement 70(1):230–234 (1992). PSA has been shown to be expressed in normal prostate glands, as well as in cancerous prostate glands. Moreover, while elevated levels of PSA indicate an increased likelihood of the presence of prostate cancer, such elevated levels are also found in a high percentage of patients with benign prostatic hyperplasia and other benign urological disorders. Somewhat improved differentiation between prostate cancer and benign prostatic hyperplasia has been reported if the level of PSA-ACT (α1-antichymotrypsin) complex present in patient serum is measured rather than if PSA levels alone are measured. Stenman et al., Cancer Res. 51:222–261 (1991), Lilja et al., Clin. Chem. 37:1618–1625 (1991); Christensson et al., J. Urology 150:100–105 (1993). This procedure too, however, is not highly specific for prostate cancer. There is a need for an accurate diagnostic method that can distinguish between prostate cancer and benign prostatic hyperplasia.

SUMMARY OF THE INVENTION

It is an object of the invention to provide a safe, accurate, easy test for diagnosing prostate cancer.

It is yet another object of the invention to provide a diagnostic assay for prostate cancer that can distinguish between prostate cancer and benign prostatic hyperplasia.

It is yet another object of the invention to provide a non-surgical diagnostic assay for prostate cancer.

It is yet another object of the invention to provide a test for prostate cancer by assaying serum from a patient.

It is yet another object of the invention to provide an assay for monitoring the progression of prostate cancer.

It is yet another object of the invention to provide an assay for monitoring the effect of therapy for prostate cancer.

It is yet another object of the invention to provide an assay for the presence of residual prostate cancer after radical prostatectomy.

It is yet another object of the invention to provide a diagnostic assay for prostate cancer which involves measuring the level of prostate cancer specific ACT in the serum of a patient.

It is yet another object of the invention to provide an assay for determining prostate cancer specific ACT levels by adding PSA and measuring the amount of PSA-ACT complex that is formed.

According to the invention, a method for diagnosing prostate cancer in a mammal is provided. Serum is provided from the mammal. PSA is added to this serum, and the amount of ACT-PSA complex formed is measured, e.g., by chromatography, e.g., Superdex or Sephacryl, electrophoresis, capillary electrophoresis, solid phase affinity or immunoassay, e.g., using antibodies, monoclonal or polyclonal, against, e.g., PSA or ACT. (So far, there is not available a monoclonal antibody against the PSA-ACT complex. However, when one becomes available, it should be usable in this assay.) It is determined if the mammal has prostate cancer based on the mount of ACT-PSA complex that is formed.

In certain embodiments, the PSA is added in an amount sufficient to bind to substantially all ACT that can bind to PSA under conditions which permit ACT-PSA complex formation, e.g., in an mount at least of about 500 ng/ml to about 2000 ng/ml, preferably in an mount from about 1000 ng/ml to about 2000 ng/ml. Preferably, the ACT-PSA complex formation is allowed to proceed, e.g., at a temperature from about 32° C. to about 37° C., and, e.g., for about 2 hours to about 4 hours. Variations of the method include fractionating the serum prior to adding PSA to the serum.

Another aspect of the invention is a method for differentiating prostate cancer serum from benign prostatic hyperplasia serum or normal serum. Prostate cancer serum, benign prostatic hyperplasia serum, normal serum and test serum are provided. PSA is added to each of these sera. The amount of ACT-PSA complex formed with each of these sera is measured. It is determined if the test serum is prostate cancer serum, benign prostatic hyperplasia serum or normal serum by the amount of ACT-PSA complex formed. Yet another aspect of the invention is a method for measuring a prostate cancer specific form of ACT. A test sample of ACT is provided. This ACT is contacted with PSA, and the amount of ACT-PSA complex formed is measured. It is determined if the test sample of ACT is prostate cancer specific ACT by the amount of ACT-PSA complex that is formed.

Still another aspect of the invention is an isolated cancer specific form of ACT that is capable of forming a stable complex with PSA, preferably at temperatures from about 32° C. to about 37° C., preferably in periods of about 2 to about 4 hours. This ACT has a molecular weight of about 60–66 kDa and is a variant of the known normal sequence (see Chandra eta., 1983; Hill et at., 1984; Rubin et at., 1990).

The above and other objects, features and advantages of the present invention will be better understood from the following specification.

DETAILED DESCRIPTION

Figure 1:
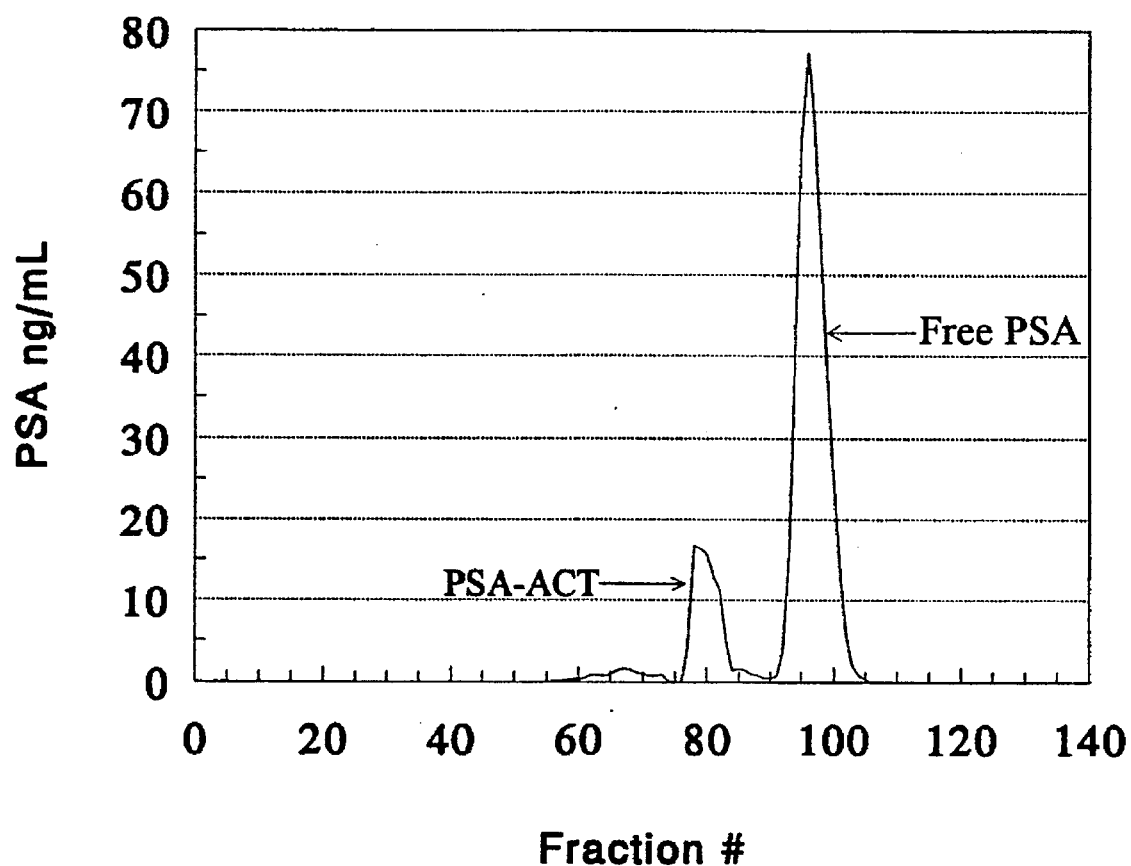
FIGS. 1–3 show the elution profile of added PSA in sera from prostate cancer, BPH and normal patients, respectively.

This invention provides a method for diagnosing prostate cancer in a mammal. Serum is provided from the mammal. PSA is added to this serum, and the amount of ACT-PSA complex formed is measured. It is determined if the mammal has prostate cancer based on the amount of ACT-PSA complex that is formed.

Prostate cancer is a disease which affects males. It is meant to include, but not be limited to, adeno-carcinoma, undifferentiated prostatic carcinoma, squamous cell carcinoma and ductal transitional carcinoma. Diagnosing prostate cancer is meant to include, e.g., diagnosing the presence of the disease, monitoring the progression of the disease, monitoring the effect of any administered therapy, monitoring the recurrence of the disease after remission or surgery, and measuring any residual prostate cancer after surgical treatment, e.g., radical prostatectomy. By mammals is meant human as well as non-human mammals.

Serum includes, e.g., whole blood serum, and plasma or tissue extract. The serum that is used can be untreated serum or it can be treated serum, e.g., fractionated serum in which certain components, e.g., albumin, free PSA, have been removed, or serum in which certain materials have been added, e.g., sodium azide, antibiotics. The serum may or may not contain α1-antichymotrypsin (ACT).

PSA is prostate specific antigen (Wang et al 1982) It may be an active or inactive precursor (zymogen) of a 33 kilodalton serine proteinase. PSA is a single chain glycoprotein that is produced within the prostatic secretory epithelium. The PSA used in this invention can be isolated from the body, e.g., from seminal fluid, blood or prostatic tissue, or can be made synthetically, e.g., chemically or by recombinant DNA means, as known by those skilled in the art. Preferably, the PSA used is substantially pure and enzymatically active (at least 40% of it).

The PSA, when contacted with ACT, is such as to be able to form an ACT-PSA complex. Preferably, the PSA is added in an amount sufficient to bind to substantially all the ACT that is present in the serum being tested under conditions which permit ACT-PSA complex formation. It is preferable that the PSA is added in an amount that is about 4-fold to about 8-fold in excess of the amount of ACT that is present in the serum. Most preferably, it is added in an amount that is about 5-fold to about 6-fold in excess. In certain embodiments, the PSA is added in an mount at least of about 0.5 µg/mL to about 2 µg/mL, preferably about 1 µg/mL to about 1.5 µg/mL.

Conditions which permit ACT-PSA complex formation include appropriate temperature, time, shaking and absence of Tris, PMSF (phenylmethylsulfonyl fluoride) or its analog in the reaction mixture. PSA can be added to the serum and allowed to form ACT-PSA Complexes at, e.g., temperatures from about 32° C. to about 37° C., preferably from about 35° C. to about 37° C. In certain embodiments, a sequence of different temperature ranges is used, e.g., about 32° C. to about 34° C., followed by about 23° C. to about 25° C., followed by about 3° C. to about 5° C. Preferably, an initial temperature of about 32° C. is used, followed by about 23° C., followed by about 4° C. Preferably, the ACT-PSA complex formation is allowed to go to completion. In certain embodiments, the complex formation is allowed to proceed for about 50 hours to about 60 hours. Complex formation can proceed under conditions where the samples are shaken, are stationary, or are shaken and stationary in some sequence. A preferred sequence is to be stationery, followed by being shaken. In a preferred embodiment, the mixture of PSA and serum is incubated for about 2 hours at 32° C. without shaking, followed by shaking for about 8 hours at 23° C., followed by shaking for about 48 hours at 4° C.

The amount of ACT-PSA complex formed is measured by any assay known to those skilled in the art for measuring such a complex, e.g., by chromatography, electrophoresis, centrifugation, solid phase affinity, immunoassay or densitometry of Western blots. Preferred forms of chromatography include, e.g., molecular sieve chromatography, e.g., Superdex, Sephacryl and ion-exchange chromatography. See Example 1 for an embodiment which uses Superdex chromatography. Immunoassays can be performed using antibodies, e.g., polyclonal or monoclonal, against, e.g., PSA or ACT or PSA-ACT complex. Preferred immunoassays are an immunofluorometric assay, chemiluminescent assay and RIA. (Leinonen et at., 1993; Zhou et at., 1993) Based on the amount of ACT-PSA complex that is formed, it is determined if the mammal has prostate cancer. Prostate cancer serum gives higher levels of ACT-PSA complex than non-prostate cancer serum.

The invention also includes a method for differentiating prostate cancer serum from benign prostatic hyperplasia serum or normal serum. Prostate cancer serum, benign prostatic hyperplasia serum, normal serum and test serum are provided. PSA is added to each of these sera. The amount of ACT-PSA complex formed with each of these sera is measured. It is determined if the test serum is prostate cancer serum, benign prostatic hyperplasia serum or normal serum by the amount of ACT-PSA complex formed.

The determination of the type of serum present in the test serum is a function of the amount of ACT-PSA complex that is formed. High levels are formed if the test serum is prostate cancer serum, whereas low or negligible levels are formed if the test serum is benign prostatic hyperplasia serum or normal serum.

The invention further provides a method for measuring a prostate cancer specific form of ACT. A test sample of ACT is provided. This ACT is contacted with PSA, and the amount of ACT-PSA complex formed is measured. It is determined if the test sample of ACT is prostate cancer specific ACT by the amount of said ACT-PSA complex formed.

Prostate cancer specific ACT is a form of ACT which is produced by mammals having prostate cancer. Prostate cancer specific ACT is preferentially capable of forming a stable complex with PSA, as compared to non-prostate cancer specific ACT, e.g., benign prostatic hyperplasia ACT or normal ACT.

In another aspect, the invention also includes an isolated cancer specific form of ACT. Preferably, this ACT is isolated from a person with prostate cancer, e.g., from serum from this person. The ACT can also be synthesized chemically or by recombinant DNA means, as is known to those skilled in the art. This specific form of ACT is a variant of the known sequence (for known sequence, see Chandra et at., 1983; Hill et at., 1984; Rubin et at., 1990). By variant is meant a form of ACT which is capable of forming a stable complex with PSA. The specific form of ACT has a molecular weight of about 60 to 66 kDa. The specific form of ACT is capable of forming a stable complex with PSA. Such complexes are preferably formed at temperatures from about 32° C. to about 37° C., and in periods of about 4 hours to about 8 hours. The ACT-PSA complex is soluble in aqueous media and stable to SDS treatment at 100° C.

EXAMPLES

Example 1

Method for Determining the Amount of ACT-PSA Complex Present In Sera From Normal, Benign Prostatic Hyperplasia and Prostate Cancer Patients This example illustrates that PSA forms complexes with ACT from serum from prostate cancer patients, but does not form any significant amount of complexes from serum from normal or benign prostatic hyperplasia patients.

20 µL of pure free PSA solution (1 µg/20 µL) (a reference material obtained from Stanford University, purified in the laboratory of Professor Thomas Stamey using the method of Sensabaugh and Blake (1990)), reconstituted with phosphate buffered saline, was added to 1 mL of each of the following:

(1) 6% BSA-PBS buffer (6% bovine serum albumin (BSA), 50 mM disodium phosphate, 150 mM sodium chloride, 0.1% sodium azide in deionized water, pH 7.4, 0.2μ filtered);

(2) normal female serum (obtained from screened healthy blood donor);

(3) normal male serum (obtained from screened healthy blood donor);

(4) benign prostatic hyperplasia (BPH) patient serum (obtained from MD Anderson Cancer Center, Houston, Tex.);

(5) prostate cancer (PCa) patient serum (obtained from MD Anderson Cancer Center, Houston, Tex.).

Before addition of the PSA, (500 μL of the PCa patient serum was fractionated through a Superdex column. A Superalex 200 (Pharmacia, Sweden) column (90×1.5 cms) was equilibrated with elution buffer, and between the runs the column was cleaned by passing 0.25N sodium hydroxide solution through the column. The sera from normal male, normal female and BPH patient was not fractionated before addition of the PSA because total PSA in normal male and BPH patient sera was 1.13 and 0.08 ng/ml, respectively. After fractionation, this small quantity of PSA would be distributed in more than 50 fractions and would be diluted below the sensitivity limit of the total PSA assay.

After addition of the pure free PSA, samples were vortexed and incubated for 2 hours at 32° C., left at room temperature for 8 hours on a shaker, followed by 48 hours at 4° C. All samples were stored in a chromatography refrigerator (3°–4° C.) until fractionation. The samples were fractionated on a Superdex 200 column as described above. To keep the quantity of sera applied on the column constant after addition of the PSA, and to compensate for the increase in volume (1 mL to 1.02 mL), 510 mL of all incubated samples was applied on the Superdex column (instead of 500 μL serum as before addition of PSA solution).

A Bio-Rad Econo fraction collector system was used. The flow rate of the peristaltic pump and fraction volume was kept constant throughout the experiment: flow rate was 0.1 mL/min (display on the pump), fraction volume was 1.1 mL (measured after the fractionation).

Figure 2:
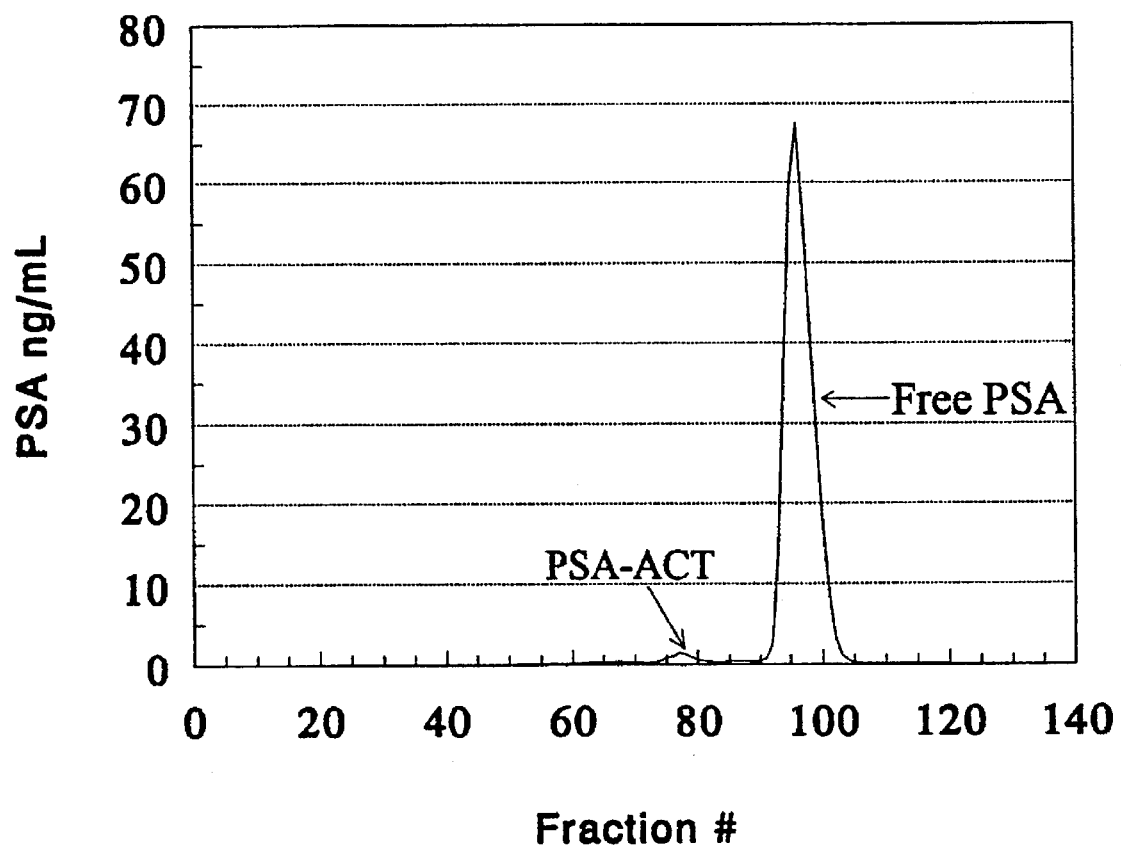
Figure 3:
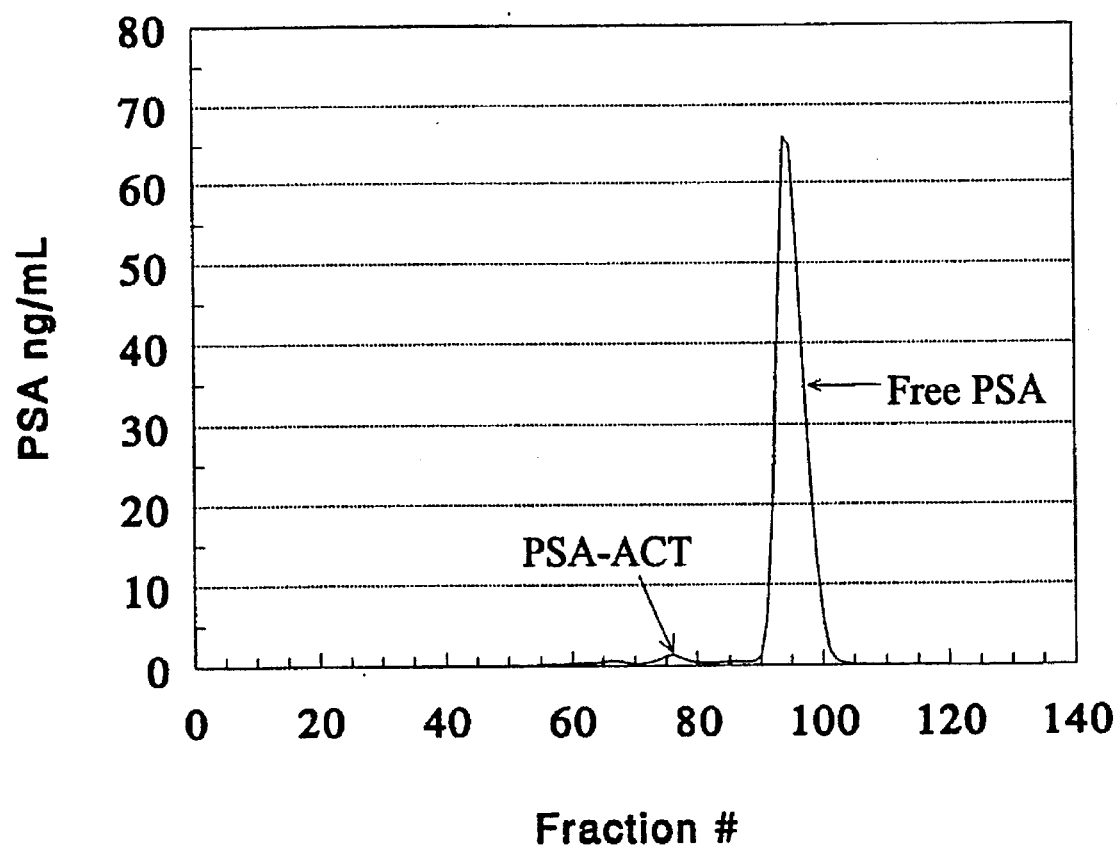

After passing through the Superdex column, proteins of the sample were separated based on their molecular weight. Free PSA was eluted from the column at approximately 30,000 Dalton and PSA-ACT complex was eluted at approximately 95,000 Dalton. FIG. 1 shows elution profile of added PSA in prostate cancer patient serum. FIG. 2 and 3 demonstrate elution profile of added PSA in BPH and normal sera, respectively. The elution buffer used was: 50 mM disodium phosphate, 150 mM sodium chloride, 0.02% BSA, 0.1% sodium azide, 0.1% Triton X-100 in deionized water, pH 6.9, 0.2μ filtered and degassed. Total PSA was measured in every fraction using the ACS PSA assay. (Bluestein et at., 1993; Zhou et at., 1994) The ACS PSA assay recognizes both free and complexed forms of PSA. Total PSA under the 30,000 and 95,000 Dalton peaks were integrated to quantify free PSA and PSA-ACT complex, respectively.

To calculate the distribution of the added PSA in PCa patient serum, peak integration values before addition of PSA were subtracted from peak integration values after addition of PSA.

Tables 1 and 2 show the results of testing the patient samples:

TABLE 1

Total PSA (ng) in Integrated Peaks

|  | Free PSA | PSA-ACT Complex |
| --- | --- | --- |
| PSA added to 6% BSA-PBS buffer | 992.7 | 5.6 |
| PSA added to normal female serum | 355.1 | 7.6 |
| PSA added to normal male serum | 373.9 | 10.0 |
| PSA added to BPH patient serum | 379.6 | 10.2 |
| PSA added in PCa patient serum | 456.4 | 72.0 |

TABLE 2

Peak Integration Before and After Addition of PSA in PCa Patient Serum

| Sample | Free PSA | PSA-ACT Complex |
| --- | --- | --- |
| PCa serum neat (before) | 51.4 | 299.8 |
| PCa serum + PSA (after) | 507.8 | 371.8 |

The PCa patient serum already had 299.8 ng complexed PSA (in 0.5 mL) and still it was able to form complex with 72 ng of added PSA. BPH and normal male had total PSA of 0.08 and 1.13 ng/ML, respectively; and after incubation with free PSA both had complexed PSA 10 ng (in 0.5 mL, peak integration).

Even though a large excess of ACT is present in BPH and normal male sera (Laurell and Jeppsson, 1975; Hinds et at., 1994), the PSA formed complexes with ACT only in the PCa patient serum. Such a result is because a PCa specific form of ACT which forms a complex with PSA is present only in the prostate cancer patient serum.

Example 2

Purification and Isolation of Cancer-specific ACT

The cancer-specific ACT is purified and isolated using procedures similar to those used by Keesee et at., PNAS 91:1913–1916 (1994). Serum from a BPH and a prostate cancer patient are fractionated through a Superdex column. All fractions containing proteins from 50–70 kDa molecular weight are pooled and concentrated. The concentrated pool is subjected to two dimensional electrophoresis, where the first dimension is isoelectric focusing and the second dimension is SDS-PAGE. These gels are probed with silver stain. The staining pattern of BPH and prostate cancer patient sera is compared and the form which is absent in BPH serum and present in cancer patient serum will be extracted from the gel. This pure prostate cancer specific form of ACT is used to raise a monoclonal antibody against this form without any cross-reactivity with normal ACT. This monoclonal antibody is used in developing an immunoassay against cancer-specific ACT. This assay does not require the addition of PSA since it probes and measures specific ACT (both complexed and free), not the PSA-ACT complex.

Further characterization experiments are conducted. After 2-D electrophoresis, proteins are transferred to a nitrocellulose membrane and probed with polyclonal antibodies against ACT that recognizes all forms of ACT. Comparison of Western blots of 2-D gel of sera from BPH and prostate cancer patients further confirm the identity of prostate cancer specific ACT. Once substantial quantities of the cancer specific form of ACT are isolated and further characterized, it can be purified using techniques like ion-exchange- and affinity-chromatography and preparative- and capillary-electrophoresis, and the sequence of the purified material can be determined.

Those skilled in the art will be able to ascertain, using no more than routine experimentation, many equivalents of the specific embodiments of the invention described herein. These and all other equivalents are intended to be encompassed by the following claims.

What is claimed is:

1. A method for diagnosing prostate cancer in a mammal, comprising:

providing serum from said mammal;

adding PSA to said serum;

measuring the amount of ACT-PSA complex formed;

determining if said mammal has prostate cancer based on the amount of said ACT-PSA complex that is formed.

2. The method of claim 1 wherein said PSA is added in an amount sufficient to bind to substantially all ACT that can bind to said PSA under conditions which permit said ACT-PSA complex formation.

3. The method of claim 1 wherein said PSA is added in an amount at least of about 500 to about 1000 ng/mL.

4. The method of claim 1 wherein said PSA is added to said serum and said ACT-PSA complex formation is allowed to proceed at a temperature from about 32° C. to about 37° C.

5. The method of claim 1 further comprising allowing said ACT-PSA complex formation to proceed for about 4 hours to about 8 hours after said PSA is added to said serum.

6. The method of claim 1 wherein said measuring is by an assay selected from the group consisting of chromatography, electrophoresis, centrifugation, solid phase affinity, densitometry of Western blot and immunoassay.

7. The method of claim 1 wherein said measuring is by chromatography selected from the group consisting of Superdex, Sephacryl and other gel permeation media.

8. The method of claim 1 wherein said measuring is by immunoassay using antibodies against compounds selected from the group consisting of PSA, ACT and the PSA-ACT complex.

9. The method of claim 8 wherein said antibodies are selected from the group consisting of monoclonal and polyclonal antibodies.

10. The method of claim 1 further comprising fractionating said serum prior to contacting said serum with said PSA.

11. A method for differentiating prostate cancer serum from benign prostatic hyperplasia serum or normal serum, comprising:

providing prostate cancer serum, benign prostatic hyperplasia serum, normal serum and test serum;

adding PSA to each of said sera;

measuring the amount of ACT-PSA complex formed with each of said sera;

determining if said test serum is prostate cancer serum, benign prostatic hyperplasia serum or normal serum by the amount of said ACT-PSA complex formed.

12. A method for measuring a prostate cancer specific form of ACT, comprising:

providing a test sample of ACT;

contacting said ACT with PSA;

measuring the amount of ACT-PSA complex formed;

determining if said test sample of ACT is prostate cancer specific ACT by the amount of said ACT-PSA complex formed.

* * * * *